(12) United States Patent
Shogbon et al.

(10) Patent No.: US 8,241,907 B2
(45) Date of Patent: Aug. 14, 2012

(54) SYNTHETIC SURFACES FOR CULTURING STEM CELL DERIVED CARDIOMYOCYTES

(75) Inventors: Christopher Bankole Shogbon, Corning, NY (US); Yue Zhou, Horseheads, NY (US); Ralph Brandenberger, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 308 days.

(21) Appl. No.: 12/362,190

(22) Filed: Jan. 29, 2009

(65) Prior Publication Data

US 2009/0191633 A1    Jul. 30, 2009

Related U.S. Application Data

(60) Provisional application No. 61/062,921, filed on Jan. 30, 2008.

(51) Int. Cl.
*C12N 5/00* (2006.01)
*C12N 5/02* (2006.01)
*C12N 5/07* (2010.01)
*C12N 5/10* (2006.01)

(52) U.S. Cl. ........ 435/395; 435/396; 435/354; 435/363; 435/366

(58) Field of Classification Search .................... 435/395
See application file for complete search history.

(56) References Cited

U.S. PATENT DOCUMENTS

| | | |
|---|---|---|
| 4,578,079 A | 3/1986 | Ruoslahti et al. |
| 4,792,525 A | 12/1988 | Ruoslahti et al. |
| 4,908,236 A | 3/1990 | Pitt et al. |
| 5,278,063 A | 1/1994 | Hubbell et al. |
| 5,330,911 A | 7/1994 | Hubbell et al. |
| 5,480,953 A | 1/1996 | Sugaya et al. |
| 5,543,318 A | 8/1996 | Smith et al. |
| 5,643,561 A | 7/1997 | Katsuen et al. |
| 5,691,203 A | 11/1997 | Katsuen et al. |
| 5,695,997 A | 12/1997 | Ruoslahti et al. |
| 5,733,727 A | 3/1998 | Field |
| 5,843,780 A | 12/1998 | Thomson |
| 5,916,875 A | 6/1999 | Ruoslahti et al. |
| 5,928,943 A | 7/1999 | Franz et al. |
| 5,942,435 A * | 8/1999 | Wheeler .................. 435/325 |
| 6,015,671 A | 1/2000 | Field |
| 6,099,832 A | 8/2000 | Mickle et al. |
| 6,110,459 A | 8/2000 | Mickle et al. |
| 6,121,027 A | 9/2000 | Clapper et al. |
| 6,245,566 B1 | 6/2001 | Gearhart et al. |
| 6,261,836 B1 | 7/2001 | Cech et al. |
| 6,306,922 B1 | 10/2001 | Hubbell et al. |
| 6,316,522 B1 | 11/2001 | Loomis et al. |
| 6,387,369 B1 | 5/2002 | Pittenger et al. |
| 6,399,300 B1 | 6/2002 | Field |
| 6,458,589 B1 | 10/2002 | Rambhatla et al. |
| 6,514,734 B1 | 2/2003 | Clapper et al. |
| 6,534,052 B1 | 3/2003 | Xiao et al. |
| 6,534,130 B1 | 3/2003 | Maag et al. |
| 6,897,271 B1 | 5/2005 | Domschke et al. |
| 7,067,194 B2 | 6/2006 | Mao et al. |
| 7,368,420 B1 | 5/2008 | Walsh |
| 7,384,984 B2 | 6/2008 | Lewandowski et al. |
| 7,402,339 B2 | 7/2008 | Schmidt et al. |
| 7,425,448 B2 | 9/2008 | Xu |
| 7,452,718 B2 | 11/2008 | Gold et al. |
| 2001/0039316 A1 | 11/2001 | Campbell et al. |
| 2002/0061837 A1 | 5/2002 | Lough, Jr. et al. |
| 2002/0142457 A1 | 10/2002 | Umezawa et al. |
| 2002/0146678 A1 | 10/2002 | Benvenisty |
| 2003/0029418 A1 | 2/2003 | Deschamps et al. |
| 2003/0083389 A1 | 5/2003 | Kao et al. |
| 2003/0180268 A1 | 9/2003 | Atala |
| 2003/0215946 A1 | 11/2003 | Nair et al. |
| 2004/0005701 A1 | 1/2004 | Xu et al. |
| 2004/0022367 A1 | 2/2004 | Talalai |
| 2005/0019747 A1 | 1/2005 | Anderson et al. |
| 2005/0036980 A1 | 2/2005 | Chaney et al. |
| 2005/0037489 A1 | 2/2005 | Gepstein et al. |
| 2005/0054092 A1 | 3/2005 | Xu et al. |
| 2005/0059150 A1 | 3/2005 | Guarino et al. |
| 2005/0136536 A1 | 6/2005 | Anderson et al. |
| 2005/0164382 A1 | 7/2005 | Xu |
| 2005/0214938 A1 | 9/2005 | Xu et al. |
| 2005/0227353 A1 | 10/2005 | Mummery |
| 2005/0265980 A1 | 12/2005 | Chen et al. |
| 2005/0266554 A1 | 12/2005 | D'Amour et al. |
| 2005/0276858 A1 | 12/2005 | Kao et al. |
| 2005/0281857 A1 | 12/2005 | Heyer et al. |
| 2006/0100369 A1 | 5/2006 | Kao et al. |

(Continued)

FOREIGN PATENT DOCUMENTS

AU    729377    2/2001

(Continued)

OTHER PUBLICATIONS

Xu et al. (Stem Cells & Development, 15: 931-941, 2006.*
Stem Cells: Scientific Progress and Future Research Directions, Department of Health and Human Services, Chapter 1, pp. 1-4, Jun. 2001.*
Anderson, D. et al., "Nanoliter-scale synthesis of arrayed biomaterials and application to human embryonic stem cells," *Nature Biotech.* 22(7) 2004, 863-6.
Barber, T. et al., "Ligan density characterization of peptide-modified biomaterials," *Biomaterials* 26 2005, 6897-905.
Barber, T. et al., "Peptide-modified p(AAm-co-EG/AAc) IPNs grafted to bulk titanium modulate osteoblast behavior in vitro," *J. Biomed. Mater. Res.* 64A 2003, 38-47.

(Continued)

*Primary Examiner* — Valarie Bertoglio
(74) *Attorney, Agent, or Firm* — Law Office of Salvatore Arrigo and Scott Lee, LLP

(57) ABSTRACT

Synthetic surfaces suitable for culturing stem cell derived cardiomyocytes contain acrylate polymers formed from one or more acrylate monomers. The acrylate surfaces, in many cases, are suitable for culturing stem cell derived cardiomyocytes in chemically defined media.

5 Claims, 3 Drawing Sheets

U.S. PATENT DOCUMENTS

| | | |
|---|---|---|
| 2006/0127878 A1 | 6/2006 | Salomon et al. |
| 2006/0134050 A1 | 6/2006 | Griffith et al. |
| 2006/0172415 A1 | 8/2006 | Okazaki |
| 2006/0228386 A1 | 10/2006 | Stephens et al. |
| 2006/0263878 A1 | 11/2006 | Mochitate |
| 2007/0026518 A1 | 2/2007 | Healy et al. |
| 2007/0029924 A1 | 2/2007 | Ushifusa et al. |
| 2007/0167354 A1 | 7/2007 | Kennedy et al. |
| 2007/0254378 A1 | 11/2007 | Zhang et al. |
| 2007/0269886 A1 | 11/2007 | Qian et al. |
| 2009/0017465 A1 | 1/2009 | Xu |
| 2009/0043079 A1 | 2/2009 | Chen et al. |
| 2009/0047739 A1 | 2/2009 | Xu et al. |
| 2009/0191626 A1 | 7/2009 | Shogbon et al. |
| 2009/0191627 A1 | 7/2009 | Fadeev et al. |
| 2009/0191632 A1 | 7/2009 | Fadeev et al. |
| 2009/0191633 A1 | 7/2009 | Shogbon et al. |
| 2009/0203065 A1 | 8/2009 | Gehman et al. |

FOREIGN PATENT DOCUMENTS

| | | |
|---|---|---|
| EP | 0450254 | 10/1991 |
| EP | 0614923 | 1/2000 |
| JP | 58-146280 | 8/1983 |
| JP | 59-093733 | 5/1984 |
| JP | 2001-309682 | 12/1989 |
| JP | 5-271579 | 10/1993 |
| JP | 2002-191353 | 7/2002 |
| JP | 2004-504834 | 2/2004 |
| JP | 2006-042794 | 2/2006 |
| JP | 2006-174826 | 7/2006 |
| WO | WO-88/08448 | 11/1988 |
| WO | WO-92/13066 | 8/1992 |
| WO | WO-95/14079 | 5/1995 |
| WO | WO-98/31734 | 7/1998 |
| WO | WO-99/49015 | 9/1999 |
| WO | WO-00/06701 | 2/2000 |
| WO | WO-00/70021 | 11/2000 |
| WO | WO-00/78119 | 12/2000 |
| WO | WO-01/22978 | 4/2001 |
| WO | WO-01/48151 | 7/2001 |
| WO | WO-01/51616 | 7/2001 |
| WO | WO-01/53465 | 7/2001 |
| WO | WO-01/68814 | 9/2001 |
| WO | WO-02/06373 | 1/2002 |
| WO | WO-02/09650 | 2/2002 |
| WO | WO 02/10347 | 2/2002 |
| WO | WO-02/13760 | 2/2002 |
| WO | WO-02/19893 | 3/2002 |
| WO | WO-02/30206 | 4/2002 |
| WO | WO-02/062961 | 8/2002 |
| WO | WO-02/062969 | 8/2002 |
| WO | WO-02/083864 | 10/2002 |
| WO | WO-03/006950 | 1/2003 |
| WO | WO-03/029418 | 4/2003 |
| WO | WO-2004/037164 | 5/2004 |
| WO | WO-2004/081205 | 9/2004 |
| WO | WO-2005/021634 | 3/2005 |
| WO | WO-2005/028619 | 3/2005 |
| WO | WO-2005/053621 | 6/2005 |
| WO | WO-2006/105278 | 10/2006 |
| WO | WO-2007/012144 | 2/2007 |
| WO | WO-2007/104107 | 9/2007 |
| WO | WO-2008/118392 | 10/2008 |
| WO | WO-2009/032117 | 3/2009 |
| WO | WO-2009/099555 | 8/2009 |

OTHER PUBLICATIONS

Bearinger, J. et al., "Biomolecular modification of p(AAm-co-EG/AA) IPNs supports osteoblast adhesion and phenotypic expression," *J. Biomater. Sci. Polymer Edn.* 9(7) 1998, 629-52.

Bearinger, J. et al., "P(AAm-co-EG) interpenetrating polymer networks grafted to oxide surfaces: surface characterization, protein adsorption, and cell detachment studies," *Langmuir* 13(19) 1997, 5175-83.

Braam, S. et al., "Recombinant vitronectin is a functionally defined substrate that supports human embryonic stem cell self renewal via AVB5 integrin," *Stem Cells* 26(9) 2008, 2257-65.

Brandley, B. et al., "Covalent attachment of an Arg-Gly-Asp sequence peptide to derivatizable polyacrylamide surfaces: sequence peptide to derivatizable polyacrylamide surfaces: support of fibroblast adhesion and long-term growth," *Anal. Biochem.* 172 1988, 270-8.

Cruise, G. et al., "Characterization of permeability and network structure of interfacially photopolymerized poly(ethylene glycol) diacrylate hydrogels," *Biomaterials* 19 1998, 1287-94.

Dawson, E. et al., "Biomaterials for stem cell differentiation," *Adv. Drug Delivery Rev.* 60 2008, 215-28.

Drumheller, P. et al., "Bioactive Peptides and Surface Design," *Interfacial Phenomena and Bioproducts*, J.L. Brash et al., *Marcel Dekker, Inc.* 1996, 273-310.

Drumheller, P. et al., "Multifunctional poly(ethylene glycol) semi-interpenetrating polymer networks as highly selective adhesive substrates for bioadhesive peptide grafting," *Biotechnol. Bioeng.* 43 1994, 772-80.

Drumheller, P. et al., "Polymer networks with grafted cell adhesion peptides for highly biospecific cell adhesive substrates," *Anal. Biochem.* 222 1994, 380-8.

Drumheller, P. et al., "Surface immobilization of adhesion ligands for investigations of cell/substrate interactions," *The Biomedical Engineering Handbook*, J.D. Bronzino, Ed., CRC & IEEE Press 1995, 1583-96.

Fittkau, M. et al., "The selective modulation of endothelial cell mobility on RGD peptide containing surfaces by YIGSR peptides," *Biomaterials* 26 2005, 167-74.

Harbers, G. et al., "Development and characterization of a high-throughput system for assessing cell-surface receptor-ligand engagement," *Langmuir* 21(18) 2005, 8374-84.

Harbers, G. et al., "The effect of ligand type and density on osteoblast adhesion, proliferation and matrix mineralization," *J. Biomed. Mater. Res.* 75A 2005, 855-69.

Healy, K. et al., "Designing biomaterials to direct biological responses," *Ann. NY Acad. Sci.* 875 1999, 24-35.

Healy, K. et al., "Molecular engineering of materials for bioreactivity," *Curr. Op. Solid State Mater. Sci.* 4 1999, 381-7.

Heggli, M. et al., "Michael-type addition as a tool for surface functionalization," *Bioconj. Chem.* 14 2003, 967-73.

Hern, D. et al., "Incorporation of adhesion peptides into nonadhesive hydrogels useful for tissue resurfacing," *J. Biomed. Mater. Res.* 39 1998, 266-76.

Hubbell, J., "Biomaterials in tissue engineering," *Biotechnol.* 13 1995, 565-76.

Hubbell, J. et al., "Surface-grafted cell-binding peptides in tissue engineering of the vascular graft," *Ann. NY Acad. Sci.* 665 1992, 253-8.

Huebsch, N. et al., "Analysis of sterilization protocols for peptide-modified hydrogels," *J. Biomed. Mater. Res.* 74B(1) 2005, 440-7.

Irwin, E. et al., "Analysis of interpenetrating polymer networks via quartz crystal microbalance with dissipation monitoring," *Langmuir* 21(12) 2005, 5529-36.

Kim, S.-Y. et al., "Synthesis and characterization of injectable poly)N-isopropylacrylamide-co-acrylic acid) hydrogels with proteolytically degradable cross-links," *Biomacromolecules* 4 2003, 1214-23.

Kim, S.-Y. et al., "Synthetic MMP-13 degradable ECMs based on poly(N-isopropyl acrylamide-co-acrylic acid) semi interpenetrating polymer networks L degradation and cell migration," *J. Biomed. Mater. Res.* 75A(1) 2005, 73-88.

Kolhar, P. et al., "Synthetic Surfaces for Human Embryonic Stem Cell Adhesion, Proliferation and Culture," Abstract submitted to 2009 AIChE Conference, 1 page (Jun. 2009).

Li, Y. et al., "Expansion of human embryonic stem cells in defined serum-free medium devoid of animal-derived products," *Biotechnol. Bioeng.* 91(6) 2005, 688-98.

Li, Y-J. et al., "Hydrogels as artificial matrices for human embryonic stem cell self-renewal," *J. Biomed. Mater. Res. Part A* 79(1) 2006, 1-5.

Lu, J. et al., "Defined culture conditions of human embryonic stem cells," *Proc. Natl. Acad. Sci. USA* 103(15) 2006, 5688-93.

Ludwig, T. et al., "Derivation of human embryonic stem cells in defined conditions," *Nat. Biotechnol.* 24(2) 2006, 185-7.

Lutolf, M. et al., "Synthesis and physicochemical characterization of end-linked poly(ethylene glycol)-co-peptide hydrogels formed by Michael-type addition," *Biomacromolecules* 4 2003, 713-22.

Lutolf, M. et al., "Synthetic biomaterials as instructive extracellular microenvironments for morphogenesis in tissue engineering," *Nature Biotechnol.* 23 2005, 47-55.

Massia, S. et al., "An RGD spacing of 440nm is sufficient for integrin alpha V beta 3-mediated fibroblast spreading and 140nm for focal contact and stress fiber formation," *J. Cell Biol.* 114 1991, 1089-100.

Massia, S. et al., "Covalently immobilized laminin peptide Tyr-Ile-Gly-Ser-Arg (YIGSR) supports cell spreading and co-localization of the 67-kilodalton laminin receptor with alpha-actinin and vinculin," *J. Biol. Chem.* 268 1993, 8053-9.

Massia, S. et al., "Human endothelial cell interactions with surface-coupled adhesion peptides on a nonadhesive glass substrate and two polymeric biomaterials," *J. Biomed. Mater. Res.* 25 1991, 223-42.

Massia, S. et al., "Immobilized amines and basic amino acids as mimetic heparin-binding domains for cell surface proteoglycan-mediated adhesion," *J. Biol. Chem.* 267 1992, 10133-41.

Massia, S. et al., "Vascular endothelial cell adhesion and spreading promoted by the peptide REDV of the IIICS region of plasma fibronectin is mediated by integrin alpha 4 beta 1," *J. Biol. Chem.* 267 1992, 14019-26.

Miskon, A. et al., "Beating behavior of primary neonatal cardiomyocytes and cardiac-differentiated P19.CL6 cells on different extracellular matrix components," *J. Artif. Organs* 12 2009, 111-7.

Model, M. et al., "Quantification of the surface density of a fluorescent label with the optical microscope," *J. Biomed. Mater. Res.* 50 2000, 90-6.

Park, S. et al., "Nanoparticulate DNA packaging using terpolymers of poly(lysine-g-lactide-b-ethylene glycol)," *Bioconjugate Chem.* 14(2) 2003, 311-9.

Park, S. et al., "Surface modification of poly(ethylene terephthalate) angioplasty balloons with a hydrophilic poly(acrylamide-co-ethylene glycol) interpenetrating network coating," *J. Biomed. Mater. Res.* 53(5) 2000, 568-76.

Pratt, A. et al., "Synthetic extracellular matrices for in situ tissue engineering," *Biotechnol. Bioeng.* 86(1) 2004, 27-36.

Rezania, A. et al., "A probabilistic approach to measure the strength of bone cell adhesion to chemically modified surfaces," *Ann. Biomed. Eng.* 25 1997, 190-203.

Rezania, A. et al., "Bioactivation of metal oxide surfaces: I. Surface characterization and cell response," *Langmuir* 15 1999, 6931-9.

Rezania, A. et al., "Biomimetic peptide surfaces that regulate adhesion, spreading, cytoskeletal organization and mineralization of the matrix deposited by osteoblast-like cells," *Biotechnol. Progress* 15(1) 1999, 19-32.

Rezania, A. et al., "Biomolecular surface engineering of materials for controlling bone cell adhesion and spreading," *Mater. Res. Soc. Symp. Proc.* 530 1998, 99-103.

Rezania, A. et al., "Integrins subunits responsible for adhesion of human osteoblast-like cells to biomimetic peptide surfaces," *J. Ortho. Res.* 17(4) 1999, 615-23.

Rezania, A. et al., "The detachment strength and morphology of bone cells contacting materials modified with a peptide sequence found within bone sialoprotein," *J. Biomed. Mater. Res.* 37(1) 1997, 9-19.

Rezania, A. et al., "The effect of peptide surface density on mineralization of a matrix deposited by osteogenic cells," *J. Biomed. Mater. Res.* 52 2000, 595-600.

Saha, K. et al., "Biomimetic interfacial interpenetration polymer networks control neural stem cell behavior," *J. Biomed. Mater. Res.* 81A(1) 2007, 240-9.

Skottman, H. et al., "Culture conditions for human embryonic stem cells," *Reprod.* 132(5) 2006, 691-8.

Stile, R. et al., "Axisymmetric adhesion test to examine the interfacial interactions between biologically-modified networks and models of the extracellular matrix," *Langmuir* 19 2003, 1853-60.

Stile, R. et al., "Poly(N-isopropylacrylamide)-based semi-interpenetrating polymer networks for tissue engineering application effects of linear poly(acrylic acid) chains on phase behavior," *Biomacromolecules* 3 2002, 591-600.

Stile, R. et al., "Poly(N-isopropylacrylamide)-based semi-interpenetrating polymer networks for tissue engineering applications. Effects of linear poly(acrylic acid) chains on rheology," *J. Biomater. Sci. Polym. Ed.* 15(7) 2004, 865-78.

Stile, R. et al., "Synthesis and characterization of injectable poly(N-isopropylacrylamide)-based hydrogels that support tissue formation in vitro," *Macromolecules* 32 1999, 7370-9.

Stile, R. et al., "Thermo-responsive peptide-modified hydrogels for tissue regeneration," *Biomacromolecules* 2 2001, 185-94.

Stojkovic, P. et al., "Human-serum matrix supports undifferentiated growth of human embryonic stem cells," *Stem Cells* 23(7) 2005, 895-902.

Thomas, C. et al., "Materials designed to control and examine the function of single cells," *Mater. Res. Soc. Symp. Proc.* 530 1998, 55-8.

Whang, K. et al., "A biodegradable polymer scaffold for delivery of osteotropic factors," *Biomaterials* 21 2000, 2545-51.

Amit, M. et al., "Feeder-free culture of human embryonic stem cells", *Meth. Enzymol.* 420 (2006), pp. 37-49.

Derda, R. et al., "Defined substrates for human embryonic stem cell growth identified from surface arrays", *ACS Chem. Biol.* 2(5) (2007), pp. 347-355.

"Alpha-1 adrenergic receptor definition," *Wikipedia entry* Mar. 26, 2009, 4 pages.

"Isoprenaline," *Wikipedia entry* Mar. 25, 2009, 2 pages.

Alsan, B. et al., "Regulation of avian cardiogenesis by Fgf8 signaling," *Development* 129 2002, 1935-43.

Andree, B. et al., "BMP-2 induces ectopic expression of cardiac lineage markers and interferes with somite formation in chicken embryos," *Mech. Dev.* 70 1998, 119-31.

Antin, P. et al., "Regulation of avian precardiac mesoderm development by insulin and insulin-like growth factors," *J. Cell. Physiol.* 168 1996, 42-50.

Arai, A. et al., "Murine cardiac progenitor cells require visceral embryonic endoderm and primitive streak for terminal differentiation," *Dev. Dynamics* 210 1997, 344-53.

Barron, M. et al., "Requirement for BMP and FGF signaling during cardiogenic induction in non-precardiac mesoderm is specific, transient, and cooperative," *Dev. Dynamics* 218 2000, 383-93.

Bauwens, C. et al., "Development of a perfusion fed bioreactor for embryonic stem cell-derived cardiomyocyte generation: oxygen-mediated enhancement of cardiomyocyte output," *Biotechnol. Bioeng.* 90(4) 2005, 452-61.

Behfar, A. et al., "Stem cell differentiation requires a paracrine pathway in the heart," *FASEB J.* 16 2002, 1558-66.

Boheler, K. et al., "Differentiation of pluripotent embryonic stem cells into cardiomyocytes," *Circ. Res.* 91 2002, 189-201.

Caspi, O. et al., "Potential applications of human embryonic stem cell-derived cardiomyocytes," *Ann. NY Acad. Sci.* 1015 2004, 285-98.

Cerbai, E. et al., "Electrophysiologic effects of lercanidipine on repolarizing potassium currents," *J. Cardiovasc. Pharmacol.* 36 (2000), pp. 584-591.

Charron, F. et al., "GATA transcription factors and cardiac development," *Sem. Cell Dev. Biol.* 10 (1999), pp. 85-91.

Claycomb, W. et al., "HL-1 cells: A cardiac muscle cell line that contracts and retains phenotypic characteristics of the adult cardiomyocyte," *Proc. Natl. Acad. Sci. USA* 95 1998, 2979-84.

Corsini, A. et al., "Effect of the new calcium antagonist lercanidipine and its enantiomers on the migration and proliferation of arterial myocytes," *J. Cardiovasc. Pharmacol.* 28 1996, 687-94.

Cowan, D. et al., "The regulation of glutathione peroxidase gene expression by oxygen tension in cultured human cardiomyocytes," *J. Mol. Cell. Cardiol.* 24(4) (1992), pp. 423-433.

Czyz, J. et al., "Potential of embryonic and adult stem cells in vitro," *Biol. Chem.* 384 (2003), pp. 1391-1409.

Dang, S. et al., "Controlled, scalable embryonic stem cell differentiation culture," *Stem Cells* 22(3) (2004), pp. 275-282.

De Pater, E. et al., "Distinct phases of cardiomyocyte differentiation regulate growth of the zebrafish heart," *Development* 136 (2009), pp. 1633-1641.

Doevendans, P. et al., "Differentiation of cardiomyocytes in floating embryoid bodies is comparable to fetal cardiomyocytes," *J. Mol. Cell Cardiol.* 32 2000, 839-51.

Dubus, I. et al., "Contractile protein gene expression in serum-free cultured adult rat cardiomyocytes," *Plfugers Arch* 423 1993, 455-61.

Feng, J. et al., "Antisense oligodeoxynucleotides direccted against Kv1.5 mRNA specifically inhibit ultrarapid delayed rectifier K+ current in cultured adult human atrial myocytes," *Circ. Res.* 80 (1997), pp. 572-579.

Fukuda, K., "Development of regenerative cardiomyocytes from mesenchymal stem cells for cardiovascular tissue engineering," *Artificial Organs* 25(3) 2001, 187-93.

Gepstein, L., "Derivation and potential applications of human embryonic stem cells," *Circ. Res.* 91(10) 2002, 866-76.

Gerecht-Nir, S. et al., "Vascular gene expression and phenotypic correlation during differentiation of human embryonic stem cells," *Dev. Dyn.* 232 (2005), pp. 487-497.

Ginis, I. et al., "Differences between human and mouse embryonic stem cells," *Dev. Biol.* 269 2004, 360-80.

Goh, G. et al., "Molecular and phenotypic analyses of human embryonic stem cell-derived cardiomyocytes," *Thromb. Haemost.* 94 2005, 728-37.

Goldman, B. et al., "Epidermal growth factor promotes a cardiomyoblastic phenotype in human fetal cardiac myocytes," *Exp. Cell Res.* 228 (1996), pp. 237-245.

Goldman, B. et al., "Human fetal cardiocytes in enriched culture," *In Vitro Cell. Dev. Biol.—Animal* 31 1995, 731-4.

Grepin, C. et al., "Enhanced cardiogenesis in embryonic stem cells overexpressing the GATA-4 transcription factor," *Development* 124 1997, 2387-95.

Gryshchenko, O. et al., "Outwards currents in embryonic stem cell-derived cardiomyocytes," *Pflugers Arch Eur. J. Physiol.* 439 2000, 798-807.

Heng, B. et al., "Strategies for directing the differentiaion of stem cells into the cardiomyogenic lineage in vitro," *Cardiovascular Res.* 62 2004, 34-42.

Itskovitz-Eldor, J. et al., "Differentiation of human embryonic stem cells into embryoid bodies comprising the three embryonic germ layers," *Mol. Med.* 6(2) (2000), pp. 88-95.

Johansson, B. et al., "Evidence for involvement of activin A and bone morphogenetic protein 4 in mammalian mesoderm and hematopoietic development," *Molec. Cell. Biol.* 15(1) (1995), pp. 141-151.

Kawai, T. et al., "Efficient cardiomyogenic differentiation of embryonic stem cell by fibroblast growth factor 2 and bone morphogenetic protein 2," *Circ. J.* 68 2004, 691-702.

Kehat, I. et al., "Electromechanical integration of cardiomyocytes derived from human embryonic stem cells," *Nature Biotechnol.* 22(10) (2004), pp. 1282-1289.

Kehat, I. et al., "Human embryonic stem cells can diffrentiate into myocytes with structural and functional properties of cardiomyocytes," *J. Clin. Invest.* 108(3) 2001, 407-14.

Kehat, I. et al., "Long term high-resolution, electrophysiological assessment of human embryonic stem cell derived cardiomyocytes: A novel in vitro model for the human heart," *Circulation* 102(18 Suppl. II) Abstract 6 2000, II-4.

Kessler, P. et al., "Myoblast cell grafting into heart muscle: Cellular biology and potential applications," *Annu. Rev. Physiol.* 61 1999, 219-42.

Khamsi, R., "Geneticists Hail Variety Show, Map of DNA Differences will Help Experts Tailor Drugs," *Nature*, online Oct. 26, 2005, 2 pages.

Khamsi, R., "Market Watch," *Nature* 437 (2005), p. 1231.

Klug, M. et al., "Genetically selected cardiomyocytes from differentiating embryonic stem cells from stable intracardiac grafts," *J. Clin. Invest.* 98 (1996), pp. 216-224.

Koide, M. et al., "Atrial natriuretic peptide accelerates proliferation of chick embryonic cardiomyocytes in vitro," *Differentiation* 61 1996, 1-11.

Kolossov, E. et al., "Functional characteristics of ES cell-derived cardiac precursor cells identified by tissue-specific expression of the green fluorescent protein," *J. Cell Biol.* 143(7) 1998, 2045-56.

Ladd, A. et al., "Regulation of avian cardiac myogenesis by activin/TGFÃ¢ and bone morphogenetic proteins," *Dev. Biol.* 204 1998, 407-19.

Laflamme, M. et al., "Formation of human myocardium in the rat heart from human embryonic stem cells," *Am. J. Pathol.* 167(3) 2005, 663-71.

Lev, S. et al., "Differentiation pathways in human embryonic stem cell-derived cardiomyocytes," *Ann. N.Y. Acad. Sci.* 1047 2005, 50-65.

Li, R-K. et al., "Isolation of Cardiomyocytes from Human Myocardium for Primary Cell Culture," *J. Tiss. Culture Meth.* 15 1993, 147-54.

Liechty, K. et al., "Human mesenchymal stem cells engraft and demonstrate site-specific differentiation after in utero transplantation in sheep," *Nature Med.* 6 2000, 1282-6.

Lim, J. et al., "Proteosome analysis of conditioned medium from mouse embryonic fibroblast feeder layers which support the growth of human embryonic stem cells," *Proteomics* 2 (2002), pp. 1187-1203.

Lough, J. et al., "Combined BMP-2 and FGF-4, but neither factor alone, induces cardiogenesis in non-precardiac embryonic mesoderm," *Dev. Biol.* 178 1996, 198-202.

Makino, S. et al., "Cardiomyocytes can be generated from marrow stromal cells in vitro," *J. Clin. Invest.* 103 1999, 697-705.

Maltsev, V. et al., "Embryonic stem cells differentiate in vitro into cardiomyocytes representing sinusnodal, atrial and ventricular cell types," *Mech. Dev.* 44 1993, 41-50.

Marvin, M. et al., "Inhibition of Wnt activity induces heart formation from posterior mesoderm," *Genes Dev.* 15 2001, 316-27.

Matsushita, T. et al., "Formation of cell junctions between grafted and host cardiomyocytes at the border zone of rat myocardial infarction," *Circulation* 100(Suppl. II) 1999, II-262-8.

McBurney, M. et al., "Control of muscle and neuronal differentiation in a cultured embryonal carcinoma cell line," *Nature* 299 1982, 165-7.

McDowell, N. et al., "Activin as a morphogen in Xenopus mesoderm induction," *Seminars in Cell & Devel. Biol.* 10 1999, 311-7.

Menard, C. et al., "Transplantation of cardiac-committed mouse embryonic stem cells to infarcted sheep myocardium: preclinical study," *The Lancet* 366 2005, 1005-12.

Messina, E. et al., "Isolation and expansion of adult cardiac stem cells from human and murine heart," *Circ. Res.* 95 2004, 911-21.

Min, J-Y. et al., "Transplantation of embryonic stem cells improves cardiac function in postinfacted rats," *J. Appl. Physiol.* 92 2002, 288-96.

Monzen, K. et al., "Bone morphogenetic proteins induce cardiomyocyte differentiation through the mitogen-activated protein kinase kinase kinase TAK1 and cardiac transcription factors Csx/Nkx-2.5 and GATA-4," *Mol. Cell Biol.* 19(10) 1999, 7096-105.

Muller, M. et al., "Selection of ventricular-like cardiomyocytes from ES cells in vitro," *FASEB J.* 14 2000, 2540-8.

Mummery, C. et al., "Cardiomyocyte differentiation of mouse and human embryonic stem cells," *J. Anat.* 200 2002, 233-242.

Mummery, C. et al., "Differentiation of human embryonic stem cells to cardiomyocytes: Role of coculture with visceral endoderm-like cells," *Circulation* 107 2003, 2733-40.

Murrell, W. et al., "On the ontogeny of cardiac gene transcripts," *Mech. Ageing & Dev.* 77 1994, 109-26.

Murry, C. et al., "Muscle cell grafting for the treatment and prevention of heart failure," *J. Card. Failure* 8(6 Supp) 2002, S532-S541.

Muslin, A. et al., "Well-defined growth factors promote cardiac development in axolotl mesodermal explants," *Development* 112 1991, 1095-1101.

Nair, P. et al., "Selective use of calcium chelators enhances the yield of calcium-tolerant myocytes from adult heart," *Indian J. Exp. Biol.* 35(5) 1 page Abstract 1997, 451-6.

Narita, N. et al., "Cardiomyocyte differentiation by GATA-4-deficient embryonic stem cells," *Development* 122 1996, 3755-64.

Odorico, J. et al., "Multilineage differentiation from human embryonic stem cell lines," *Stem Cells* 19 2001, 193-204.

Oh, H. et al., "Cardiac progenitor cells from adult myocardium: Homing, differentiation, and fusion after infarction," *Proc. Natl. Acad. Sci. USA* 100(21) 2003, 12313-8.

Oh, S. et al., "Human embryonic stem cells: technological challenges towards therapy," *Clin. Exp. Pharmacol. Physiol.* 33 (2006), pp. 489-495.

Olson, E. et al., "Molecular pathways controlling heart development," *Science* 272 1996, 671-5.

O'Shea, K., "Embryonic Stem Cell Models of Development," *Anatomical Record (New Anat.)* 257(1) 1999, 32-41.

Pandur, P., "What does it take to make a heart?," *Biol. Cell* 97 2005, 197-210.

Piao, S. et al., "A simplified method for identification of human cardiac myosin heavy-chain isoforms," *Biotechnol. Appl. Biochem.* 37 (2003), pp. 27-30.

Qin, L. et al., "Gene transfer of transforming growth factor-Ã¢1 prolongs murine cardiac allograft survival by inhibiting cell-mediated immunity," *Hum. Gene Therapy* 7 1996, 1981-8.

Reubinoff, B. et al., "Embryonic stem cells lines from human blastocysts: somatic differentiation in vitro," *Nat. Biotech.* 18 (2000), pp. 399-404.

Rice, N. et al., "Skeletal myosin heavy chain function in cultured lung myofibroblasts," *J. Cell. Biol.* 163(1) 2003, 119-29.

Satin, J. et al., "Mechanism of spontaneous excitability in human embryonic stem cell derived cardiomyocytes," *J. Physiol.* 559(2) 2004, 479-96.

Scalia, P. et al., "Regulation of the Akt/Glycogen synthase kinase-3 axis by insulin-like growth factor-II via activation of the human insulin receptor isoform-A," *J. Cell. Biochem.* 82 2001, 610-8.

Schlange, T., "BMP2 is required for early heart development during a distinct time period," *Mech. Dev.* 91 2000, 259-70.

Schneider, V. et al., "Wnt antagonism initiates cardiogenesis in Xenopus laevis," *Genes Dev.* 15 2001, 304-15.

Schuldiner, M. et al., "Effects of eight growth factors on the differentiation of cells derived from human embryonic stem cells," *Proc. Natl. Acad. Sci. USA* 97(21) (2000), pp. 11307-11312.

Schultheiss, T. et al., "A role for bone morphogenetic proteins in the induction of cardiac myogenesis," *Genes Dev.* 11 1997, 451-62.

Schultheiss, T. et al., "Induction of avian cardiac myogenesis by anterior endoderm," *Development* 121 1995, 4203-14.

Shamblott, M. et al., "Derivation of pluripotent stem cells from cultured human primordial germ cells," *Proc. Natl. Acad. Sci. USA* 95 (1998), pp. 13726-13731.

Shi, Y. et al., "BMP signaling is required for heart formation in vertebrates," *Dev. Biol.* 224 2000, 226-37.

Skerjanc, I. et al., "Myocyte enhancer factor 2C and Nkx2-5 upregulate each other's expression and initiate cardiomygenesis in P19 cells," *J. Biol. Chem.* 273(52) 1998, 34904-19.

Strauer, B. et al., "Stem Cell Therapy in Perspective," *Circulation* 107 2003, 929-34.

Sugi, Y. et al., "Activin-A and FGF-2 mimic the inductive effects of anterior endoderm on terminal cardiac myogenesis in Vitro," *Dev. Biol.* 168 1995, 567-74.

Symes, K. et al., "Morphological differences in Xenopus embryonic mesodermal cells are specified as an early response to distinct threshold concentrations of activin," *Development* 120 1994, 2339-46.

Takahashi, K. et al., "Taurine renders the cell resistant to ischemia-induced injury induced in cultured neonatal rat cardiomyocytes," *J. Cardiovasc. Pharmacol.* 41 2003, 726-33.

Thomson, J. et al., "Embryonic stem cell lines derived from human blastocysts," *Science* 282 (1998), pp. 1145-1147.

Thomson, J. et al., "Isolation of a primate embryonic stem cell line," *Proc. Natl. Acad. Sci. USA* 92 (1995), pp. 7844-7848.

Tweedie, D. et al., "The effect of alterations to action potential duration on Beta-adrenoceptor-mediated aftercontractions in human and guinea-pig ventricular myocytes," *J. Mol. Cell Cardiol.* 29 (1997), pp. 1457-1467.

Van Laake, L. et al., "Cardiomyocytes derived from stem cells," *Ann. Med.* 37 2005, 499-512.

Velez, C. et al., "Modulation of contractile protein troponin-T in chick myocardial cells by basic fibroblast growth factor and platelet-derived growth factor during development," *J. Cardiovasc. Pharmacol.* 24 1994, 906-13.

Verfaillie, C. et al., "Stem Cells: Hype and Reality," *Hematology Am. Soc. Hematol. Educ. Program* (2002), pp. 369-391.

Vogel, G., "Researchers get green light for work on stem cells," *Science* 289(5484) (2000), pp. 1442-1443.

Vogel, G., "Wisconsin to distribute embryonic cell lines," *Science* 287(5455) (2000), pp. 948-949.

Volz, A. et al., "Longevity of adult ventricular rat heart muscle cells in serum-free primary culture," *J. Mol. Cell Cardiol.* 23 1991, 161-73.

Walters, M. et al., "Bone morphogenetic protein function is required for terminal differentiation of the heart but not for early expression of cardiac marker genes," *Mech. Dev.* 100 2001, 263-73.

Wobus, A. et al., "Development of cardiomyocytes expressing cardiac-specific genes, action potentials, and ionic channels during embryonic stem cell-derived cardiogenesis," *Ann. N.Y. Acad. Sci.* 752 1995, 460-9.

Wobus, A. et al., "In Vitro cellular models for cardiac development and pharmacotoxicolgy," *Toxic. in Vitro* 9 1995, 477-88.

Wobus, A. et al., "Retinoic acid accelerates embryonic stem cell-derived cardiac differentiation and enhances development of ventricular cardiomyocytes," *J. Mol. Cell Cardiol.* 29 (1997), pp. 1525-1539.

Wu, T. et al., "Effect of sodium tanshinone IIA sulfonate in the rabbit myocardium and on human cardiomyocytes and vascular endothelial cells," *Biochem. Pharmacol.* 46(12) (1993), pp. 2327-2332.

Xiao, Y.-F. et al., "Cardiac application of embryonic stem cells," *Acta Physiologica Sinica* 55(5) 2003, 493-504.

Xu, C. et al., "Cardiac Bodies: A novel culture method for enrichment of cardiomyocytes derived from human embryonic stem cells," *Stem Cells & Dev.* 15 2006, 631-9.

Xu, C. et al., "Characterization and enrichment of cardiomyocytes derived from human embryonic stem cells," *Circ. Res.* 91(6) (2002), pp. 501-508.

Xu, C. et al., "Feeder-free growth of undifferentiated human embryonic stem cells," *Nature Biotech.* 19 (2001), pp. 971-974.

Xu, C. et al., "Specific arrest of cardiogenesis in cultured embryonic stem cells lacking Cripto-1," *Dev. Biol.* 196 1998, 237-47.

Yatskievych, T. et al., "Induction of cardiac myogenesis in avian pregastrula epiblast: the role of the hypoblast and activin," *Development* 124 1997, 2561-70.

Zandstra, P. et al., "Scalable production of embryonic stem cell-derived cardiomyocytes," *Tissue Eng.* 9(4) 2003, 767-78.

Zhu, X. et al., "Evidence that fibroblast growth factors 1 and 4 participate in regulation of cardiogenesis," *Dev. Dynamics* 207 1996, 429-38.

Zingg, J.-M. et al., "Genetic and epigenetic aspects of DNA methylation on genome expression, evolution, mutation and carcinogenesis," *Carcinogenesis* 18(5) 1997, 869-82.

Iida, K. et al., "Expression of MEF2 genes duringh human cardiac development", *Tohoku J. Exp. Med.* 187(1) (1999), pp. 15-23.

Besse, D. et al., "Synthesis of selenocysteine peptides and their oxidation to diselenide-bridged compounds", *J. Pept. Sci.* 3(6), (1997), pp. 442-453.

Cowan, C. et al., "Derivation of embryonic stem-cell lines from human blastocysts", *N. Engl. J. Med.* 350(13), 2004, pp. 1353-1356.

Fassler, R. et al., "Lack of beta-1 integrin gene in embryonic stem cells affects morphology, adhesion, and migration but not integration into the inner cell mass of blastocysts", *J. Cell Biol.* 128(5), (1995), pp. 979-988.

Hayes, B. et al., "Derivation, characterization, and in vitro differentiation of canine embryonic stem cells", *Stem Cells* 26, (2008), pp. 465-473.

Horak, D. et al., "Poly(2-hydroxyethyl methacrylate)-based slabs as a mouse embryonic stem cell support", *Biomaterials* 25(22), (2004), pp. 5249-5460.

Klimanskaya, I. et al., "Human embryonic stem cells derived without feeder cells", *Lancet* 365(9471), (2005), pp. 1636-1641.

Koide, T. et al., "Syntheses and biological activities of selenium analogs of alpha-rat atrial natriuretic peptide", *Chem. Pharm. Bull.* 41(9), (1993), pp. 1596-1600.

Koide, T. et al., "Synthetic study on selenocystine-containing peptides", *Chem. Pharm. Bull.* 41(3), (1993), pp. 502-506.

Kroupova, J. et al., "Functional polymer hydrogels for embryonic stem cell support", *J. Biomed. Mat. Res.* 76B(2), (2006), pp. 315-325.

Liu, X. et al., "Micelles and hollow nanospheres based on epsilon-caprolactone-containing polymers in aqueous media", *Angewandte Chemie* 114(16), (2002),pp. 3074-3077.

Mallon, B. et al., "Toward xeno-free culture of human embryonic stem cells", *Intl. J. Biochem. Cell Biol.* 38, ((2006)),pp. 1063-1075.

Nistor, G. et al., "Human embryonic stem cells differentiate into oligodendrocytes in high purity and myelinate after spinal cord transplantation", *Glia* 49, ((2005)),pp. 385-396.

Shin, H. et al., "Attachment, proliferation, and migration of marrow stromal osteoblasts cultured on biomimetic hydrogels modified with an osteopontin-derived peptide", *Biomaterials* 25(5), (2004),pp. 895-906.

Singh, A. et al., "Chibby, an antagonist of the Wnt/Beta-catenin pathway, facilitates cardiomyocyte differentiation of murine embryonic stem cells", *Circulation* 115, (2007),pp. 617-626.

Takahashi, K. et al., "Induction of pluripotent stem cells from adult human fibroblasts by defined factors", *Cell* 131(5), (2007),pp. 861-872.

Tanahashi, K. et al., "Protein adsorption and smooth muscle cell adhesion on biodegradable agmatine-modified poly(propylene fumarate-co-ethylene glycol) hydrogels", *J. Biomed. Mat. Res.* 67(2), (2003),pp. 448-457.

Ueda, S. et al., "Establishment of rat embryonic stem cells and making of chimera rats", *PLoS ONE* 3(7), (2009),pp. 1-9.

Wobus, A. et al., "Pluripotent mouse embryonic stem cells are able to differentiate into cardiomyocytes expressing chronotropic responses to adrenergic and cholinergic agents and Ca2+ channel blockers", *Differentiation* 48, (1991),pp. 173-182.

Yu, J. et al., "Induced pluripotent stem cell lines derived from human somatic cells", *Science* 318, (2007),pp. 1917-1920.

Zhang, Y. et al., "Oligodendrocyte progenitor cells derived from human embryonic stem cells express neurotrophic factors", *Stem Cells Dev.* 15, ((2006)),pp. 943-952.

\* cited by examiner

US 8,241,907 B2

SYNTHETIC SURFACES FOR CULTURING STEM CELL DERIVED CARDIOMYOCYTES

PRIORITY

This application claims priority to U.S. provisional Appl. No. 61/062,921, filed Jan. 30, 2008, and is incorporated by reference in its entirety.

FIELD

The present disclosure relates to cell culture articles and methods of use thereof, and more particularly to articles suitable for supporting the culture of stem cell derived cardiomyocytes.

BACKGROUND

Pluripotent stem cells such as human embryonic stem cells (hESCs) have the ability to differentiate into any of the three germ layers, giving rise to any adult cell type in the human body. This unique property provides a potential for developing new treatments for a number of serious cell degenerative diseases, such as diabetes, spinal cord injury, heart diseases and the like. For example, unlike organs such as the skin or liver, the heart is not capable of regenerate sufficient cardiomyocytes to undergo extensive repair. Therefore cardiac repair may benefit from cardiomyocytes, which can be differentiated from hESCs or other pluripotent stem cells, being transplanted into the heart.

However there remain obstacles in the development of such hESC-based treatments. Such obstacles include obtaining and maintaining adequate numbers of undifferentiated hESCs in tissue culture and controlling their differentiation in order to produce specific cell types. Stem cell cultures, such as hES cell cultures are typically seeded with a small number of cells from a cell bank or stock and then amplified in the undifferentiated state until differentiation is desired for a given therapeutic application. To accomplish this, the hESC or their differentiated cells are currently cultured in the presence of surfaces or media containing animal-derived components, such as feeder layers, fetal bovine serum, or MATRIGEL. These animal-derived additions to the culture environment expose the cells to potentially harmful viruses or other infectious agents which could be transferred to patients or compromise general culture and maintenance of the hESCs. In addition, such biological products are vulnerable to batch variation, immune response and limited shelf-life.

Some steps have been taken to culture hESCs either in media or on surfaces that are free of animal-derived components. However, the response of hESCs or their differentiated derivatives is difficult to predict as components of the surface or culture medium change. Yet some advances have been made. For example, hESC-derived cardiomyocytes have been cultured in defined serum-free medium. While such culture systems are not completely xeno-free culture systems when the matrices employed contain animal-derived components, such as gelatin and MATRIGEL, they do provide a step toward the eventual clinical application of hESC-derived cardiomyocytes. By way of further example, some synthetic surfaces have been identified that can support differentiation of human epithelial stem cells into epithelial cells. However, the systems employed relied on serum medium for the cell culture, which still potentially causes problem as described before for all biological animal derived components. To date, a completely animal free system employing a chemically defined medium and a synthetic surface has not yet been identified for culturing stem cells or cells derived from stem cells.

BRIEF SUMMARY

The present disclosure describes, inter alia, synthetic surfaces useful in the culture of stem cell-derived cardiomyocytes in chemically defined media.

In an embodiment, a method for culturing a stem cell-derived cardiomyocytes is provided. The method includes depositing a suspension containing the stem cell-derived cardiomyocyte on a polymer material and culturing the deposited stem cell-derived cardiomyocyte in a cell culture medium. The polymer material comprises a homopolymer or copolymer of selected one or more acrylate monomers.

In an embodiment, a culture of a stem cell-derived cardiomyocyte is provided. The culture includes an article having a polymeric material disposed on a surface. The culture further includes the stem cell-derived cardiomyocyte disposed on the polymer material and a culture medium in which the stem cell-derived cardiomyocyte is cultured. The polymer material comprises a homopolymer or copolymer of selected one or more acrylate monomers.

In an embodiment, a cell culture article for culturing stem cell-derived cardiomyocytes in a chemically defined medium is provided. The article includes a substrate having a surface and a polymer material disposed on the surface. The polymer material comprises a homopolymer or copolymer of selected one or more acrylate monomers.

One or more of the various embodiments presented herein provide one or more advantages over prior surfaces for culturing stem cell-derived cardiomyocytes. For example, the synthetic surfaces reduce potential contamination issues associated with surfaces having components obtained from or derived from animal sources. Such surfaces may also provide for improved shelf life compared to those surfaces with biological components. The ability to culture stem cell-derived cardiomyocytes in chemically-defined media further reduces potential contamination issues. In addition, there will likely be less batch to batch variation in the ability of the synthetic surfaces or chemically defined media, resulting in improved reproducibility of culture results and expectations. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

As used herein the term "acrylate" includes compounds containing an acrylate moiety or a methacrylate moiety. An acrylate moiety is moiety of the following formula: $CH_2CHC(O)O—$. A methacrylate moiety is a moiety of the following formula: $CH_2C(CH_3)C(O)O—$. For the purposes of this disclosure, the term "acrylate" includes specific compounds disclosed in Table 1. "Acrylate" and "methacrylate" are used herein interchangeable, except when content clearly dictates otherwise; e.g. when a specific compound or group of compounds are named.

The present disclosure describes, inter alia, articles having synthetic surfaces for culturing stem cell-derived cardiomyocytes and methods for culturing stem cell-derived cardiomyocytes on such surfaces. In some embodiments, the synthetic surfaces are used in combination with a chemically defined medium to culture stem cell-derived cardiomyocytes. The surfaces may be useful in differentiating stem cells, such as hESCs, into cardiomyocytes.

1. Cell Culture Article

Figure 1A:
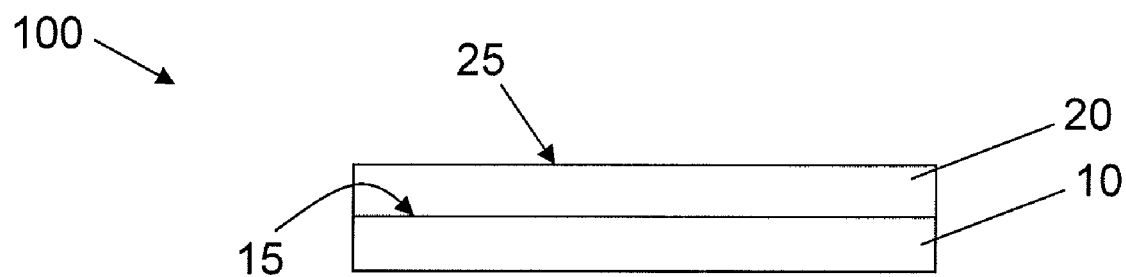
FIG. 1A-B are schematic diagrams of side views of synthetic polymer layer coated articles.

Referring to FIG. 1, a schematic diagram of article 100 for culturing cells is shown. The article 100 includes a base material substrate 10 having a surface 15. A synthetic polymer coating layer 20 is disposed on the surface 15 of the base material 10. While not shown, it will be understood that synthetic polymer coating 20 may be disposed on a portion of base material 10. The base material 10 may be any material suitable for culturing cells, including a ceramic substance, a glass, a plastic, a polymer or co-polymer, any combinations thereof, or a coating of one material on another. Such base materials 10 include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

Examples of articles 100 suitable for cell culture include single and multi-well plates, such as 6, 12, 96, 384, and 1536 well plates, jars, petri dishes, flasks, beakers, plates, roller bottles, slides, such as chambered and multichambered culture slides, tubes, cover slips, cups, spinner bottles, perfusion chambers, bioreactors, and fermenters.

Synthetic polymer coating 20 provides a surface 25 on which cells may be cultured. The synthetic polymer surface 20 includes polymerized (meth)acrylate monomers, selected from the group of monomers provided in Table 1 below. Other materials (not shown), such as peptides, may be incorporated into or conjugated to synthetic polymer surface to produce a biomimetic surface.

TABLE 1

List of acrylate and methacrylate monomers

| Monomer name | Monomer structure |
| --- | --- |
| Tetra(ethylene glycol) diacrylate | $(H_2C=CH—C(=O)—OCH_2CH_2OCH_2CH_2)_2O$ |
| Glycerol dimethacrylate | $H_2C=C(CH_3)—C(=O)—OCH_2CH(OH)CH_2O—C(=O)—C(CH_3)=CH_2$ |
| Triethylene glycol dimethacrylate | $H_2C=C(CH_3)—C(=O)—(OCH_2CH_2)_3O—C(=O)—C(CH_3)=CH_2$ |
| 1,4-Butanediol dimethacrylate | $H_2C=C(CH_3)—C(=O)—OCH_2CH_2CH_2CH_2O—C(=O)—C(CH_3)=CH_2$ |

TABLE 1-continued

List of acrylate and methacrylate monomers

| Monomer name | Monomer structure |
| --- | --- |
| Poly(ethylene glycol) diacrylate (average $M_n$~258) | $H_2C{=}CH-\overset{O}{\underset{\|}{C}}-(OCH_2CH_2)_n-O-\overset{O}{\underset{\|}{C}}-CH{=}CH_2$ |
| Di(ethylene glycol) dimethacrylate | $H_2C{=}\underset{CH_3}{\overset{\|}{C}}-\overset{O}{\underset{\|}{C}}-OCH_2CH_2OCH_2CH_2O-\overset{O}{\underset{\|}{C}}-\underset{CH_3}{\overset{\|}{C}}{=}CH_2$ |
| Tetra(ethylene glycol) dimethacrylate | $H_2C{=}\underset{\phantom{CH_3}}{\overset{CH_3}{\underset{\|}{C}}}-\overset{O}{\underset{\|}{C}}-OCH_2CH_2OCH_2CH_2OCH_2CH_2OCH_2CH_2O-\overset{O}{\underset{\|}{C}}-\underset{\phantom{CH_3}}{\overset{CH_3}{\underset{\|}{C}}}{=}C$ |
| 1,6-Hexanediol propoxylate diacrylate | $H_2C{=}CH-\overset{O}{\underset{\|}{C}}-O-(C_3H_6O)_n-CH_2CH_2CH_2$<br>$H_2C{=}CH\ \ \overset{\phantom{O}}{\underset{\|}{C}}\ \ O\ \ (C_3H_6O)_n\ \ CH_2CH_2CH_2$<br>$\phantom{H_2C{=}CH}\ \overset{\|}{O}$ |
| Neopentyl glycol diacrylate | $H_2C{=}CH-\overset{O}{\underset{\|}{C}}-OCH_2-\underset{CH_3}{\overset{CH_3}{\underset{\|}{\overset{\|}{C}}}}-CH_2O-\overset{O}{\underset{\|}{C}}-CH{=}CH_2$ |
| Neopentyl glycol dimethacrylate | $H_2C{=}\underset{CH_3}{\overset{\|}{C}}-\overset{O}{\underset{\|}{C}}-OCH_2-\underset{CH_3}{\overset{CH_3}{\underset{\|}{\overset{\|}{C}}}}-CH_2O-\overset{O}{\underset{\|}{C}}-\underset{CH_3}{\overset{\|}{C}}{=}CH_2$ |
| Trimethylolpropane benzoate diacrylate | $H_2C{=}CH-\overset{O}{\underset{\|}{C}}-OCH_2-\underset{CH_2O-\overset{\|}{\underset{\|}{C}}-\text{Ph}}{\overset{CH_2CH_3}{\underset{\|}{\overset{\|}{C}}}}-CH_2O-\overset{O}{\underset{\|}{C}}-CH{=}CH_2$ |
| Trimethylolpropane ethoxylate (1 EO/OH) methyl | $H_2C{=}CH-\overset{O}{\underset{\|}{C}}-OCH_2CH_2OCH_2$<br>$CH_3OCH_2CH_2OCH_2-\overset{\phantom{O}}{\underset{\|}{C}}CH_2CH_3$<br>$H_2C{=}CH-\overset{O}{\underset{\|}{C}}-OCH_2CH_2OCH_2$ |
| Tricyclo[5.2.1.0$^{2,6}$]decanedimethanol diacrylate | (structure shown) |
| Neopentyl glycol ethoxylate diacrylate | (structure shown with $x$ and $y$ ethoxylate units and central $C(CH_3)_2$) |

TABLE 1-continued

List of acrylate and methacrylate monomers

| Monomer name | Monomer structure |
| --- | --- |
| Trimethylolpropane triacrylate | (structure shown) |

The acrylates listed in Table 1 may be synthesized as known in the art or obtained from a commercial vendor, such as Polysciences, Inc., Sigma Aldrich, Inc., and Sartomer, Inc.

Figure 1B:
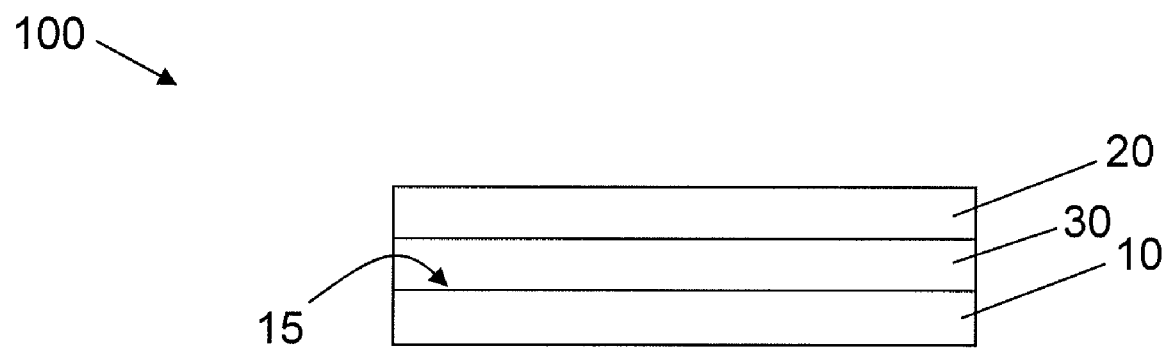

As shown in FIG. 1B, an intermediate layer 30 may be disposed between surface 15 of base material 10 and the synthetic polymer coating 20. Intermediate layer 30 may be configured to improve binding of coating 20 to substrate 10, to facilitate monomer spreading, to render portions of the surface 10 that are uncoated cytophobic to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with an epoxy coating or a silane coating. For various polymer base materials 10 it may be desirable to provide an intermediate layer 30 of polyamide, polyimide, polypropylene, polyethylene, or polyacrylate. While not shown, it will be understood that synthetic polymer coating 20 may be disposed on a portion of intermediate layer 30. It will be further understood that intermediate layer 30 may be disposed on a portion of base material 10.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency (RF) and microwave plasmas both primary and secondary, dielectric barrier discharge, and corona discharge generated in molecular or mixed gases including air, oxygen, nitrogen, argon, carbon dioxide, nitrous oxide, or water vapor.

Synthetic polymer coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. While the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Higher degrees of cross-linking may result in reduced waste product and reduced cell toxicity.

Figure 2A:
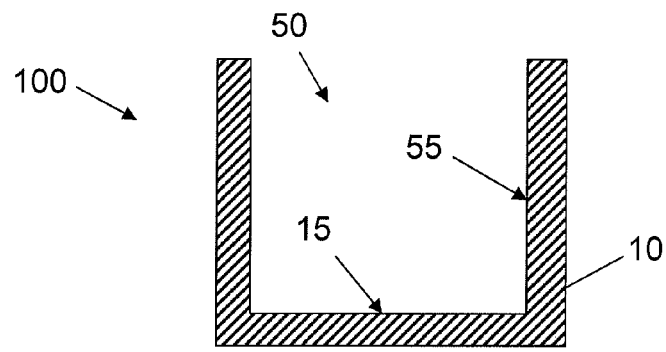
FIG. 2A-C are schematic diagrams of cross sections of a multi-well cell culture plate. The plate is uncoated in FIG. 2A and coated in FIGS. 2B-C.
Figure 2B:
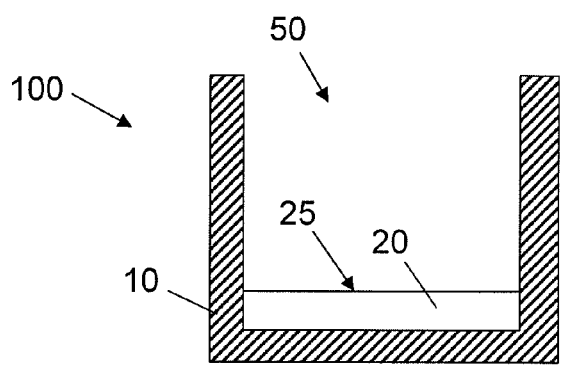
Figure 2C:
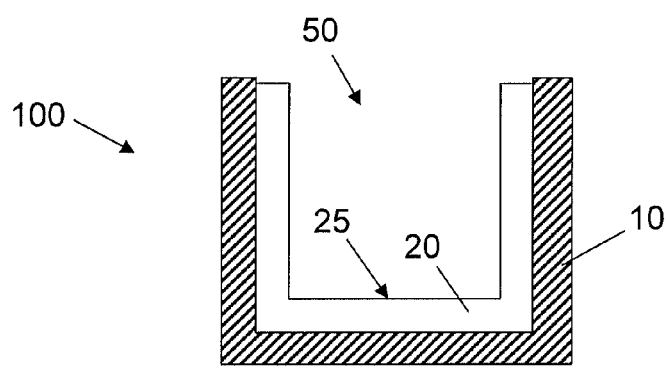

Article 100, in numerous embodiments, is cell culture ware having a well, such as a petri dish, a multi-well plate, a flask, a beaker or other container having a well. Referring now to FIG. 2, article 100 formed from base material 10 may include one or more wells 50. Well 50 includes a sidewall 55 and a surface 15. Referring to FIG. 2B-C, a synthetic polymer coating 20 may be disposed on surface 15 or sidewalls 55 (or, as discussed above with regard to FIG. 1 one or more intermediate layer 30 may be disposed between surface 15 or sidewall 55 and synthetic polymer coating 20) or a portion thereof.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

2. Coating of Synthetic Polymer Layer

A synthetic polymer layer may be disposed on a surface of a cell culture article via any known or future developed process. Preferably, the synthetic polymer layer provides a uniform layer that does not delaminate during typical cell culture conditions. The synthetic polymer surface may be associated with the base material substrate via covalent or non-covalent interactions. Examples of non-covalent interactions that may associate the synthetic polymer surface with the substrate include chemical adsorption, hydrogen bonding, surface interpenetration, ionic bonding, van der Waals forces, hydrophobic interactions, dipole-dipole interactions, mechanical interlocking, and combinations thereof.

In various embodiments, the base material substrate surface is coated according to the teachings of co-pending application Ser. No. 12/362,782, filed on even date herewith, naming Gehman et al. as inventors, and entitled STEM CELL CULTURE ARTICLE AND SCREENING, which is hereby incorporated herein by reference in its entirety for all purposes to the extent that it does not conflict with the disclosure presented herein.

In numerous embodiments, monomers are deposited on a surface of a cell culture article and polymerized in situ. In such embodiments, the base material will be referred to herein as the "substrate" on which the synthetic polymer material is deposited. Polymerization may be done in solution phase or in bulk phase.

As many of the monomers identified in Table 1 above are viscous, it may be desirable to dilute the monomers in a suitable solvent to reduce viscosity prior to being dispensed on the surface. Reducing viscosity may allow for thinner and more uniform layers of the synthetic polymer material to be formed. One of skill in the art will be able to readily select a suitable solvent. Preferably the solvent is compatible with the material forming the cell culture article and the monomers. It may be desirable to select a monomer that is non-toxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In such circumstances, it may be desirable that the solvent be readily removable without harsh conditions, such as vacuum or extreme heat. Volatile solvents are examples of such readily removable solvents.

Some solvents that may be suitable in various situations for coating articles as described herein include ethanol, isopropanol, acetyl acetate, dimethylformamide (DMF), and dimethylsulfoxide (DMSO). As described in co-pending application Ser. No. 12/362,782 ethanol may be a particularly suitable solvent when it is desired to remove solvent prior to polymerization.

The monomers may be diluted with solvent by any suitable amount to achieve the desired viscosity and monomer concentration. Generally the monomer compositions used according to the teachings presented herein contain between about 1% to about 99% monomer. By way of example, the monomer may be diluted with an ethanol solvent to provide a composition having between about 1% and about 50% monomer, or from about 1% to about 10% monomer by volume. The monomers may be diluted with solvent so that the polymer layer 20 achieves a desired thickness. As discussed above, if the deposited monomers are too thick, a non-uniform surface may result. As described in further details in the Examples, non-uniform surfaces may be observed when the monomer-solvent composition is deposited on a surface 15 of a well 50 at a volume of greater than about 8 microliters per square centimeter of the surface 15. In various embodiments, the monomer-solvent compositions are deposited on a surface 15 of a well 50 in a volume of about 7 microliters or less per square centimeter of the surface 15. For example, the monomer-solvent compositions may be deposited on a surface 15 of a well 50 in a volume of about 5 microliters or less per square centimeter of the surface 15, or about 2 microliters or less per square centimeter of the surface 15.

In various embodiments, synthetic polymer surface is deposited on a surface of an intermediate layer that is associated with the base material via covalent or non-covalent interactions, either directly or via one or more additional intermediate layers (not shown). In such embodiments, the intermediate layer will be referred to herein as the "substrate" onto which the synthetic polymer surface is deposited.

In various embodiments, the surface of the base material is treated. The surface may be treated to improve binding of the synthetic polymer surface to the base material surface, to facilitate monomer spreading on the base material surface, or the like. Of course, the base material may be treated for similar purposes with regard to an intermediate layer. In various embodiments, the surface is corona treated or vacuum plasma treated. High surface energy obtainable from such treatments may facilitate monomer spreading and uniform coating. Examples of vacuum plasma treatment that may be employed include microwave vacuum plasma treatments and radio frequency vacuum plasma treatments. The vacuum plasma treatments may be performed in the presence of reactive gases, such as oxygen, nitrogen, ammonia or nitric oxide.

To form the synthetic polymer surface, one or more monomers presented in Table 1 above are polymerized. If one monomer is used, the polymer will be referred to as a homopolymer of the monomer. If two or more different monomers are used, the polymer will be referred to as a copolymer of the monomers. The monomers employed may be monofunctional, difunctional, or higher-functional. When two or more monomers are used, the ratio of the monomers may be varied. In various embodiments, two monomers are used and the ratio, by volume of the first monomer to the second monomer ranges from between about 5:95 to about 95:5. For example, the ratio of the first monomer to the second monomer ranges from between about 10:90 to about 90:10, about 20:80 to about 80:20, from about 30:70 to about 70:30. In some embodiments, the ratio of the first monomer to the second monomer is about 50:50, 30:70, or 10:90. It will be understood that the molecular weight of the polymer may be controlled by varying the concentration of monomers or the ratios of difunctional or higher-functional monomers to monofunctional monomers. Increased concentrations of difunctional or higher-functional monomers will increase the degree of cross-linking in the chains.

In addition to the monomers that form the polymer layer, a composition forming the layer may include one or more additional compounds such as surfactants, wetting agents, photoinitiators, thermal initiators, catalysts, activators, and cross-linking agents.

Any suitable polymerization initiator may be employed. One of skill in the art will readily be able to select a suitable initiator, e.g. a radical initiator or a cationic initiator, suitable for use with the monomers listed in Table 1. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

In various embodiments where the monomers are diluted in solvent before being deposited on the substrate surface, the solvent is removed prior to polymerizing. The solvent may be removed by any suitable mechanism or process. As described in copending application Ser. No. 12/362,782 it has been found that removal of substantially all of the solvent prior to curing, allows for better control of curing kinetics and the amount of monomer converted. When conversion rates of the monomers are increased, waste generation and cytotoxicity are reduced.

Whether polymerized in bulk phase (substantially solvent free) or solvent phase, the monomers are polymerized via an appropriate initiation mechanism. Many of such mechanisms are well known in the art. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity.

The cured synthetic polymer layer may be washed with solvent one or more times to remove impurities such as unreacted monomers or low molecular weight polymer species. In various embodiments, the layer is washed with an ethanol solvent, e.g. greater than about 70% ethanol, greater than about 90% ethanol, greater than about 95% ethanol or greater than about 99% ethanol. Washing with an ethanol solvent may not only serve to remove impurities, which may be cytotoxic, but also can serve to sterilize the surface prior to incubation with cells.

3. Incubating Cells on Synthetic Polymer Layer

Stem cell-derived cardiomyocytes may be cultured on a synthetic polymer layer, as described above, according to any suitable protocol. As used herein, "stem cell derived cardiomyocyte" means a cardiomyocyte obtained from differentiation of a stem cell. In some embodiments, the stem cells are multipotent, totipotent, or pluripotent stem cells. In some embodiments the cells may be present in an organ or tissue of a subject. In numerous embodiments, the stem cells are embryonic stem cells, such as human embryonic stem cells.

Because human embryonic stem cells (hES) have the ability to grown continually in culture in an undifferentiated state, the hES cells for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) *Science* 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5): 1517-29, 2005); lines HUES 1-17 (Cowan et al., NEJM 350 (13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Cardiomyocytes according to the invention may also be differentiated from induced primate pluripotent stem (iPS) cells. iPS cells refer to cells, obtained from a juvenile or adult mammal such as a human, that are genetically modified, e.g., by transfection with one or more appropriate vectors, such that they are reprogrammed to attain the phenotype of a pluripotent stem cell such as an hES cell. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into cardiomyocytes. The iPS cells, like hES cells, also form teratomas when injected into immuno-deficient mice, e.g., SCID mice. (Takahashi et al., (2007) Cell 131(5):861; Yu et al., (2007) Science 318:5858).

Stem cell derived cardiomyocytes may be obtained by any suitable methods. One way to obtain such cells is described in Laflamme et al., "Cardiomyocytes derived from human embryonic stem cells in pro-survival factors enhance function of infracted rats, *Nature Biotechnology,* 25: 1015-1024 (2007). Briefly, undifferentiated human embryonic stem cells, such as those derived from the female H7 human embryonic stem cell line, may be seeded on MATRIGEL-coated plates at a density of about 100,000 cells/cm$^2$ and refed daily with hES cell growth medium (KO DMEM+20% Serum replacement, 1 mM l-glutamine, 1% NEAA, 0.1 mM 2-ME plus hbFGF at 80 ng/ml and TGFb1 at 0.5 ng/ml) To induce differentiation, growth media may be replaced with RPMI-B27 medium (available from Invitrogen) supplemented with about 100 ng/ml human recombinant activin A (available from R&D Systems) for about 24 hours, followed by 10 ng/ml human recombinant BMP4 (available from R&D Systems) for four days. Of course, any other suitable method may be employed (see, e.g., U.S. Pat. No. 7,425,448).

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown origin. In some embodiments, conditioned media contains polypeptides or proteins of known composition, such as recombinant growth hormones. Because all components of chemically-defined media have a known chemical structure and composition, variability in culture conditions can be reduced and thus cell response may be more reproducible. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as StemPro® a fully defined, serum- and feeder-free medium (SFM) specially formulated for the growth and expansion of human embryonic stem cells (hESCs) and StemCell Technologies, Inc as mTeSR™1 maintenance media for human embryonic stem cells.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature CO$_2$ and O$_2$ levels, growth medium, and the like, will depend on the nature of the cells being cultured and can be readily modified. The amount of time that the cells are incubated on the surface may vary depending on the cell response being studied or the cell response desired.

Any suitable method may be used, if desired, to confirm that the stem cell derived cardiomyocytes are indeed cardiomyocytes or that the stem cells employed have successfully differentiated into cardiomyocytes. For example, the presence of certain cardiomyocyte-selective markers may be investigated. Such markers include Nkx2.5 and α-actinin, cardiac troponin I. Antibodies to such markers may be used in standard immunocytochemical or flow cytometry techniques. In addition or alternatively, cellular morphology or functionality, by observing beating cardiomyocytes in culture or by performing various electrophysiological analyses to determine whether the cells have characteristics of cardiomyocytes.

The cultured stem cell derived cardiomyocytes may be used for any suitable purpose, including investigational studies in culture, in animals, for developing therapeutic uses, for drug discovery and toxicology or for therapeutic purposes. One potential therapeutic or investigational purpose is repairing cardiac damage due to an infarct, e.g., as described in Laflamme et al., *Nature Biotechnology*, 25: 1015-1024 (2007). The cells may also be used to create cDNA libraries according to known methods. The cDNA libraries may be used to study gene expression in the differentiated cardiomyocytes. For example the library obtained from the differentiated cardiomyocytes may be compared to a cDNA library from the undifferentiated stem cells from which the cardiomyocytes were derived, thus allowing for the identification and isolation of genes related to the differentiation and development of cardiomyocytes.

In the following, non-limiting examples are presented, which describe various embodiments of the articles and methods discussed above.

EXAMPLES

Example 1

Identification of Acrylic Coating Surfaces Suitable for Culturing Stem Cell Derived Cardiomyocytes in a Chemically Defined Medium 1. Coating Preparation Acrylic coating surfaces were prepared from homomonomers or copolymers of various acrylate and methacrylate monomers. For copolymers two different acrylate or methacrylate monomers were used. Briefly, the monomers were mixed with 1% w/w of photoinitiator Irgacure 819 (Ciba Specialty Chemicals, Inc.) and used along or blended with other monomer formulation (monomer with 1% w/w of photoinitiator) according to volume ratio of 70:30. Then formulation was placed in a well of a vacuum plasma treated cyclic olefin copolymer plate (provided by Corning Life Science Development group) at a volume of 2.5 μL. The plate was allowed to lay horizontally flat for 30 min for the formulation to spread out. The coatings were cured with 13 mW/cm$^2$ pulsed (100 Hz) UV light (Xenon RC-700) for 1 min in N$_2$ purged box (with fused silica window). All the plates were sterilized by 25-35 kGy Gamma radiation prior to cell culture.

2. Cell Preparation and Assays

Prior to the experiments, H7 hES cells were maintained in the undifferentiated state on MATRIGEL-coated plates in SR medium (KO-DMEM, 20% KO-serum replacement, 1 mM L-glutamine, 0.1 mM β-mercaptoethanol, 1% non-essential amino acids, 80 ng/ml hbFGF and 0.5 ng/ml TGFb1). hESC-derived cardiomyocytes were generated using direct differentiation protocol. Briefly, undifferentiated H7 cells were harvested by 200 U/ml collagenase IV and seeded on MATRIGEL-coated plates at the density of 100,000 cells/cm$^2$ in SR medium. Cells were cultured for 6 days with daily medium exchange. Cardiac differentiation was initiated by replacing SR medium with RPMI-B27 medium, supplemented with 100 ng/ml human recombinant activin A for 24 h, followed by 10 ng/ml human recombinant BMP4 for 4 days. At this point, cells were detached by Accutase treatment, re-suspended in RPMI-B27 medium w/o growth factors, and seeded at the density of 100,000 cells/cm$^2$ onto Corning CB/TOPAS 96-well plates coated with different binary mixtures of acrylates or MATRIGEL as positive control. Cells were cultured for another 2-3 weeks with the same medium exchange every 2-3 days. The wells were microscopically examined, and spontaneous beating activity was recorded.

At the end of the differentiation protocol, cells were fixed with 4% paraformaldehyde immunostained for cardiomyocyte (CM) specific markers, Nkx2.5 and α-actinin, and counterstained with 4'-6-Diamidino-2-phenylindole (DAPI) to stain the nucleus. After scanning each plate with ArrayScan, the following quantitative analyses were performed for each surface: 1) TNC: total number of cells based on DAPI positive cell number, 2) TNC: total number of CM, based on NRx2.5-positive cell number, 3) CM yield=TNC/TNC.

3. Results

It was found that only a small portion of the tested surfaces supported the cell growth while maintaining some key characteristics and functions. Examples of the coating surfaces which supported growth of differentiated human embryonic cardiomyocytes in chemically defined medium are listed in Table 2, where the volume ratio of monomer (1) to monomer (2) is 70:30. These surfaces were characterized and given a "grade" based on qualitative assessments of the morphology of the cells and their adhesion to the surfaces. Acrylate surface rating was performed based on consideration of the following criteria: 1) total cell number, 2) total CM number, 3) CM yield, 4) presence of beating areas, 5) similarity to Matrigel derived CM morphology. Notes on the qualities of the differentiated embryonic myocytes that were observed are shown in Table 3, as well as the grade that was assessed. For example, "Sim MA" is a note that indicates that cells growing on that surface were similar to cells growing on Matrigel™, "Sim TOP" is a note that indicates that the cells growing on that surface were similar to cells growing on plasma-treated cyclic olefin copolymer surface, sold as TOPAS® surface by TOPAS, Florence, Ky. The notes also indicate that some of the surfaces supported differentiated embryonic myocytes that began to beat in culture.

TABLE 2

Example compositions of acrylic polymers which support the culture of hES cell derived cardiomyocytes in chemically defined medium.

| Formuation ID | Monomer (1) | Monomer (2) |
|---|---|---|
| 95-1 | Tetra(ethylene glycol) diacrylate 100% | |
| 95-2 | Glycerol dimethacrylate 100% | |
| 90-2 | Triethylene glycol dimethacrylate 100% | |
| 90-4 | 1,4-Butanediol dimethacrylate 100% | |
| 95-3 | Poly(ethylene glycol) diacrylate 100% | |
| 122-1 | Tetra(ethylene glycol) diacrylate 70% | Glycerol dimethacrylate 30% |
| 122-3 | Tetra(ethylene glycol) diacrylate 70% | 1,4-Butanediol dimethacrylate 30% |
| 27-2 | Tetra(ethylene glycol) diacrylate 70% | Trimethylolpropane triacrylate 30% |
| 123-1 | Glycerol dimethacrylate 70% | Tetra(ethylene glycol) diacrylate 30% |
| 123-2 | Glycerol dimethacrylate 70% | Tri(ethylene glycol) dimethacrylate 30% |
| 123-3 | Glycerol dimethacrylate 70% | 1,4-Butanediol dimethacrylate 30% |
| 123-4 | Glycerol dimethacrylate 70% | Poly(ethylene glycol) diacrylate 30% |
| 123-6 | Triethylene glycol dimethacrylate 70% | Glycerol dimethacrylate 30% |
| 123-7 | Triethylene glycol dimethacrylate 70% | 1,4-Butanediol dimethacrylate 30% |
| 124-2 | 1,4-Butanediol dimethacrylate 70% | Glycerol dimethacrylate 30% |
| 124-3 | 1,4-Butanediol dimethacrylate 70% | Triethylene glycol dimethacrylate 30% |
| 124-5 | Poly(ethylene glycol) diacrylate 70% | Tetra(ethylene glycol) diacrylate 30% |
| 133-1 | Di(ethylene glycol) dimethacrylate 70% | Tetraethylene glycol dimethacrylate 30% |
| 134-1 | Tetraethylene glycol dimethacrylate 70% | Di(ethylene glycol) dimethacrylate 30% |
| 140-1 | Trimethylolpropane triacrylate 70% | Neopentyl glycol ethoxylate diacrylate 30% |

TABLE 3

Cell count, cell surface Marker, and functions of h7 differentiated cardiomyocyted cultured on acrylate polymer surfaces.

| ID | Rating | Beating | Average Cell Count (per well) | Average % Nkx2.5 | Cardio yield (based on count*Nkx2.5) | Note |
|---|---|---|---|---|---|---|
| 95-2 | A | y | 19970 | 7 | 1397.9 | Sim MA |
| 90-2 | C− | | 5420 | 14 | 758.8 | Sim MA, peeled lumpy |
| 90-4 | B− | y | 6907 | 24 | 1657.68 | Sim TOP |
| 95-3 | C | y | 3788 | 24 | 909.12 | |
| 122-3 | B | | 6061 | 3 | 181.83 | Sim as MA, not beating |
| 123-1 | B+ | y | 5250 | 5 | 262.5 | Sim MA, beating |
| 123-2 | A | | 6327 | 7 | 442.89 | Good attachment, no beating |
| 123-3 | A | | 6223 | 8 | 497.84 | Good attachment, no beating |
| 123-4 | B− | | 4954 | 4 | 198.16 | Many attached, dying |
| 123-7 | C | | 4246 | 15 | 636.9 | peeled |
| 124-2 | A | y | 3798 | 21 | 797.58 | Sim TOP beating |
| 124-3 | B | y | 2267 | 8 | 497.84 | Sim TOP beating |
| 124-5 | C | y | 940 | 27 | 253.8 | Beating but poor attachment |
| 140-1 | B− | y | 2886 | 33 | 952.38 | Sim TOP |

Figure 3:
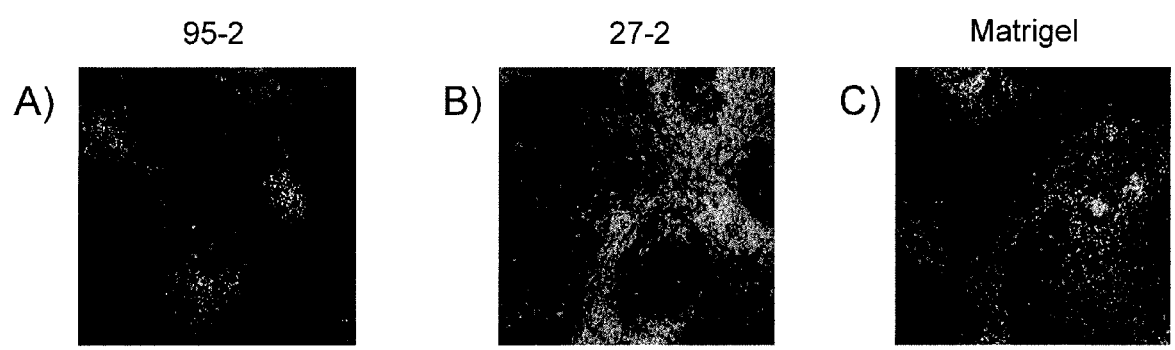
FIG. 3 is a fluorescent image of stem cell derived cardiomyocytes cultured in chemically defined medium and on a surface of formulation 1 (A), formulation 18 (B), and MATRIGEL (C) as described in Example 1. Green: Nkx 2.5. Red: Alpha-actinin.

For other tested homopolymers and copolymer combinations, very low or no cardiomyocytes yield was observed at the end of the differentiation procedure, due to either low total cell number or low Nkx2.5-positive cells present on those surfaces FIG. 3 shows fluorescent images of differentiated cardiomyocytes cultured on surfaces of formulation 95-2 (A), formulation 27-2 (B), and MATRIGEL (C). Cell morphology, Nkx 2.5 marker expression (green) and alpha-actinin marker expression (red) are similar to MATRIGEL. In addition, the cells depicted in FIG. 3 exhibited beating prior to fixing with paraformaldehyde.

Thus, embodiments of SYNTHETIC SURFACES FOR CULTURING STEM CELL DERIVED CARDIOMYOCYTES are disclosed. One skilled in the art will appreciate that the arrays, compositions, kits and methods described herein can be practiced with embodiments other than those disclosed. The disclosed embodiments are presented for purposes of illustration and not limitation.

What is claimed is:
1. A culture of a pluripotent stem cell-derived cardiomyocyte, comprising:
   an article comprising a polymeric material disposed on a surface; the pluripotent stem cell-derived cardiomyocyte disposed on the polymer material; and
   a culture medium in which the pluripotent stem cell-derived cardiomyocyte is cultured,
   wherein the polymer material comprises
   (i) tetra(ethylene glycol) diacrylate, glycerol dimethacrylate, triethylene glycol dimethacrylate, 1,4-butanediol dimethacrylate, or poly(ethylene glycol) diacrylate, or
   (ii) a copolymer formed from tetra(ethylene glycol) diacrylate and 1,4-butanediol dimethacrylate, glycerol dimethacrylate and tetra(ethylene glycol) diacrylate, glycerol dimethacrylate and tri(ethylene glycol) dimethacrylate, glycerol dimethacrylate and 1,4-butanediol dimethacrylate, glycerol dimethacrylate and poly(ethylene glycol) diacrylate, triethylene glycol dimethacrylate and 1,4-butanediol dimethacrylate, poly(ethylene glycol) diacrylate and tetra(ethylene glycol)

diacrylate, di(ethylene glycol) dimethacrylate and tetraethylene glycol dimethacrylate, tetra(ethylene glycol) diacrylate and trimethylolpropane triacrylate, trimethylolpropane triacrylate and neopentyl glycol ethoxylate diacrylate, or tetra(ethylene glycol) dimethacrylate and di(ethylene glycol) dimethacrylate.

2. The culture of claim 1, wherein the polymer material comprises a homopolymer formed from tetra(ethylene glycol) diacrylate or glycerol dimethacrylate or a copolymer formed from (i) glycerol dimethacrylate and tri(ethylene glycol) dimethacrylate, (ii) glycerol dimethacrylate and 1,4-butanediol dimethacrylate, or (iii) tetra(ethylene glycol) diacrylate and trimethylolpropane triacrylate.

3. The culture of claim 1, wherein the polymer material consists essentially of a homopolymer formed from tetra(ethylene glycol) diacrylate or glycerol dimethacrylate or a copolymer formed from (i) glycerol dimethacrylate and tri(ethylene glycol) dimethacrylate, (ii) glycerol dimethacrylate and 1,4-butanediol dimethacrylate, or (iii) tetra(ethylene glycol) diacrylate and trimethylolpropane triacrylate.

4. The culture of claim 1, wherein culture medium is a chemically defined medium.

5. The culture of claim 1, wherein the stem cell-derived cardiomyocyte is a human embryonic stem cell-derived cardiomyocyte.

* * * * *